(12) United States Patent
Brase

(10) Patent No.: US 7,803,021 B1
(45) Date of Patent: Sep. 28, 2010

(54) IMPLANTABLE ELECTRICAL STIMULATION SYSTEMS WITH LEAF SPRING CONNECTIVE CONTACTS AND METHODS OF MAKING AND USING

(75) Inventor: Randall Lee Brase, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 168 days.

(21) Appl. No.: 12/177,056

(22) Filed: Jul. 21, 2008

(51) Int. Cl.
 *H01R 24/04* (2006.01)
(52) U.S. Cl. .................. 439/668; 439/851; 439/843; 439/909
(58) Field of Classification Search .............. 439/851, 439/843, 668, 909
 See application file for complete search history.

(56) References Cited

U.S. PATENT DOCUMENTS

| | | | |
|---|---|---|---|
| 3,617,990 A * | 11/1971 | Colardeau | 439/88 |
| 4,012,103 A | 3/1977 | Lunquist | |
| 5,082,453 A | 1/1992 | Stutz, Jr. | |
| 5,304,219 A | 4/1994 | Chernoff et al. | |
| 5,328,442 A | 7/1994 | Levine | |
| 5,702,427 A | 12/1997 | Ecker et al. | |
| 5,766,042 A | 6/1998 | Ries et al. | |
| 5,769,671 A * | 6/1998 | Lim | 439/843 |
| 5,782,892 A | 7/1998 | Castle et al. | |
| 5,899,927 A | 5/1999 | Ecker et al. | |
| 5,931,861 A | 8/1999 | Werner et al. | |
| 6,181,969 B1 | 1/2001 | Gord | |
| 6,208,900 B1 | 3/2001 | Ecker et al. | |
| 6,402,793 B1 | 6/2002 | Miltich et al. | |
| 6,498,951 B1 | 12/2002 | Larson et al. | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,671,544 B2 * | 12/2003 | Baudino | 607/2 |
| 6,725,096 B2 | 4/2004 | Chinn et al. | |
| 6,741,892 B1 | 5/2004 | Meadows et al. | |
| 6,745,079 B2 | 6/2004 | King | |
| 6,878,013 B1 * | 4/2005 | Behan | 439/668 |
| 6,885,548 B2 | 4/2005 | Nyberg | |
| 7,010,351 B2 | 3/2006 | Firlik et al. | |
| 7,244,150 B1 | 7/2007 | Brase et al. | |

(Continued)

FOREIGN PATENT DOCUMENTS

WO  WO-2006/092061 A1  9/2006

OTHER PUBLICATIONS

U.S. Appl. No. 10/353,101 filed on Jan. 27, 2003.

(Continued)

*Primary Examiner*—Ross N Gushi
(74) *Attorney, Agent, or Firm*—Frommer Lawrence & Haug LLP; Patrick R. Turner

(57) ABSTRACT

An implantable control module of an electrical stimulation system includes a housing, an electronic subassembly disposed in the housing, and a plurality of conductors. The housing defines a connector receptacle configured and arranged to receive a proximal end of a lead. The housing further defines, within the connector receptacle region, a plurality of spaced-apart leaf spring connective contacts. Each leaf spring connective contact is corrugated and wrapped around at least a portion of an inner surface of the connector receptacle. Each conductor couples the electronic subassembly with at least one of the leaf spring connective contacts.

21 Claims, 9 Drawing Sheets

U.S. PATENT DOCUMENTS

| | | |
|---|---|---|
| 2003/0088274 A1 | 5/2003 | Gliner et al. |
| 2004/0059392 A1 | 3/2004 | Parramon et al. |
| 2005/0004639 A1 | 1/2005 | Erickson |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0168007 A1 | 7/2007 | Kuzma et al. |
| 2007/0239243 A1 | 10/2007 | Moffitt et al. |
| 2007/0255366 A1 | 11/2007 | Gerber et al. |
| 2008/0071320 A1 | 3/2008 | Brase |
| 2008/0103407 A1 | 5/2008 | Bolea et al. |
| 2008/0200972 A1 | 8/2008 | Rittman et al. |
| 2008/0255631 A1 | 10/2008 | Sjostedt et al. |

OTHER PUBLICATIONS

U.S. Appl. No. 10/503,281 filed on Mar. 11, 2005.
U.S. Appl. No. 11/238,240 filed on Sep. 29, 2005.

* cited by examiner

IMPLANTABLE ELECTRICAL STIMULATION SYSTEMS WITH LEAF SPRING CONNECTIVE CONTACTS AND METHODS OF MAKING AND USING

TECHNICAL FIELD

The present invention is directed to the area of implantable electrical stimulation systems and methods of making and using the systems. The present invention is also directed to implantable electrical stimulation systems that include a plurality of leaf spring connective contacts disposed in a connector receptacle to facilitate the electrical coupling of a plurality of electrodes disposed on a lead to an electronic subassembly disposed in a control module, as well as methods of making and using the leaf spring connective contacts and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, an implantable control module of an electrical stimulation system includes a housing, an electronic subassembly disposed in the housing, and a plurality of conductors. The housing defines a connector receptacle configured and arranged to receive a proximal end of a lead. The housing further defines, within the connector receptacle region, a plurality of spaced-apart leaf spring connective contacts. Each leaf spring connective contact is corrugated and wrapped around at least a portion of an inner surface of the connector receptacle. Each conductor couples the electronic subassembly with at least one of the leaf spring connective contacts.

In another embodiment, an electrical stimulating system includes a lead, a control module, and a connector receptacle. The lead has a proximal end and a distal end. The lead includes a plurality of electrodes disposed on the distal end of the lead, a plurality of contact terminals disposed on the proximal end of the lead, and a plurality of conductor wires extending along the lead to couple the electrodes electrically to the contact terminals. The control module is configured and arranged to couple to the lead and provide electrical stimulation to at least one of the electrodes. The control module includes a housing and an electronic subassembly disposed in the housing. The connector receptacle is configured and arranged to electrically couple the lead to the control module. The connector receptacle includes a plurality of spaced-apart leaf spring connective contacts and a plurality of conductors. Each leaf spring connective contact is corrugated and wrapped around at least a portion of an inner surface of the connector receptacle. Each conductor couples the electronic subassembly with at least one of the leaf spring connective contacts.

In yet another embodiment, a method for stimulating patient tissue includes implanting a lead into a patient, disposing a proximal end of the lead into a connector coupled electrically to a control module, and providing electrical signals from the control module to electrically stimulate the patient tissue. The lead includes a plurality of electrodes disposed on a distal end of the lead that are electrically coupled to at least one contact terminal disposed on the proximal end of the lead. The connector includes a plurality of leaf spring connective contacts coupled electrically to the control module. At least one leaf spring connective contact is configured and arranged to couple electrically with at least one contact terminal. Each leaf spring connective contact is corrugated and wrapped around at least a portion of an inner surface of the connector receptacle. The electrical signals provided from the control module electrically stimulate patient tissue using at least one of the electrodes.

In yet another embodiment, an implantable lead extension of an electrical stimulation system includes a housing, an electronic subassembly disposed in the housing, and a plurality of conductors. The housing defines a connector receptacle configured and arranged to receive a proximal end of a lead. The housing further defines, within the connector receptacle region, a plurality of spaced-apart leaf spring connective contacts. Each leaf spring connective contact is corrugated and wrapped around at least a portion of an inner surface of the connector receptacle. Each conductor couples the electronic subassembly with at least one of the leaf spring connective contacts.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems that include a plurality of leaf spring connective contacts disposed in a connector receptacle to facilitate the electrical coupling of a plurality of electrodes disposed on a lead to an electronic subassembly disposed in a control module, as well as methods of making and using the leaf spring connective contacts and electrical stimulation systems.

Suitable implantable electrical stimulation systems include, but are not limited to, an electrode lead ("lead") with one or more electrodes disposed on a distal end of the lead and one or more contact terminals disposed on a proximal end of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figures 1, 2:
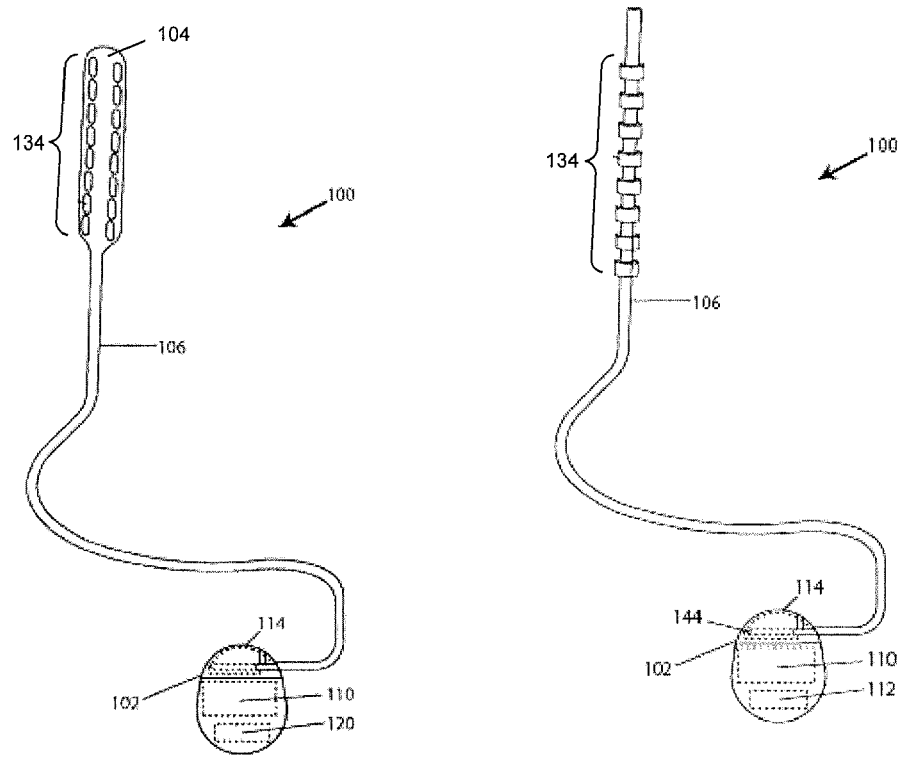
FIG. 1 is a schematic view of one embodiment of an electrical stimulation system, according to the invention.
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the lead body 106 form a lead. The paddle body 104 typically includes an array of electrodes 134. The control module 102 typically includes an electronic subassembly 110 and an optional power source 120 disposed in a sealed housing 114. The control module 102 typically includes a connector receptacle 144 (see FIGS. 2, and 3A-3B) into which the proximal end of the lead body 106 can be plugged to make an electrical connection via conductive contacts on the control module 102 and contact terminals on the lead body 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the lead body 106 and the control module 102 to extend the distance between the lead body 106 and the control module 102 of the embodiments shown in FIGS. 1 and 2.

The electrical stimulation system or components of the electrical stimulation system, including one or more of the lead body 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or lead body 106 are typically disposed in, or separated by, a non-conductive, biocompatible material including, for example, silicone, polyurethane, polyetheretherketone ("PEEK"), epoxy, and the like or combinations thereof. The paddle body 104 and lead body 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end. The non-conductive, biocompatible material of the paddle body 104 and the lead body 106 may be the same or different. The paddle body 104 and the lead body 106 may be a unitary structure or can be formed as two separate structures that are permanently or detachably coupled together.

Contact terminals (e.g., 308 in FIG. 3A and 322 of FIG. 3B) are typically disposed at the proximal end of the lead for connection to corresponding conductive contacts (e.g., 302 in FIG. 3A and 316 of FIG. 4B) in the control module 102 (or to conductive contacts on a lead extension). Conductor wires (not shown) extend from the contact terminals (e.g., 308 in FIG. 3A and 322 of FIG. 3B) to the electrodes 134. Typically, one or more electrodes 134 are electrically coupled to a contact terminal (e.g., 308 in FIG. 3A and 322 of FIG. 3B). In some embodiments, each contact terminal (e.g., 308 in FIG. 3A and 322 of FIG. 3B) is only connected to one electrode 134. The conductor wires may be embedded in the non-conductive material of the lead or can be disposed in one or more lumens 506 (e.g., lumen 506 of FIG. 5A) extending along the lead. In some embodiments, there is an individual lumen for each conductor wire. In other embodiments, two or more conductor wires may extend through a lumen. There may also be one or more lumens (e.g., lumen 504 of FIG. 5A) that open at, or near, the proximal end of the lead, for example, for inserting a stylet rod to facilitate placement of the lead within a body of a patient. Additionally, there may also be one or more lumens that open at, or near, the distal end of the lead, for example, for infusion of drugs or medication into the site of implantation of the paddle body 104.

Figure 3A:
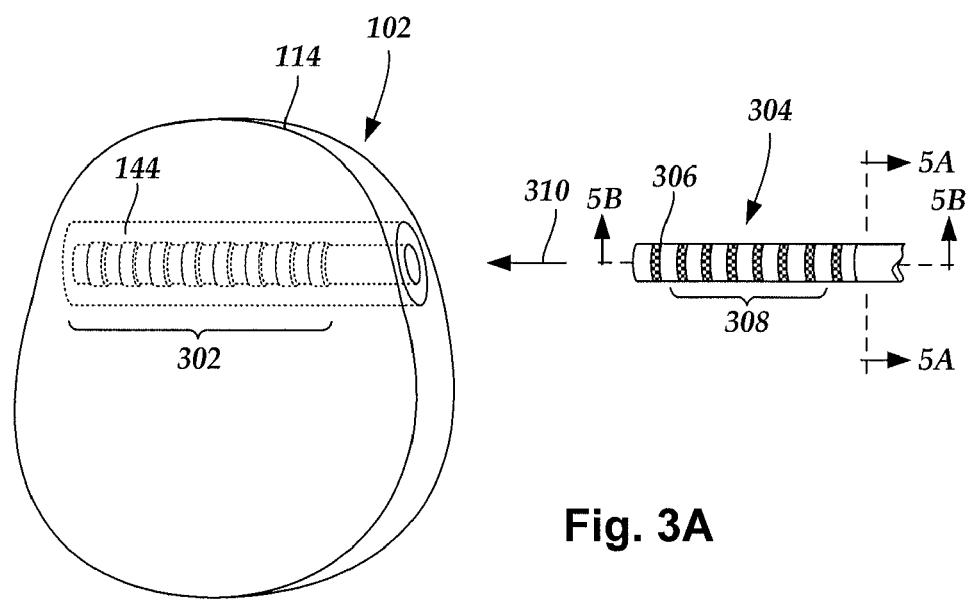
FIG. 3A is a schematic view of one embodiment of a proximal portion of a lead and a control module of an electrical stimulation system, according to the invention.

In at least some embodiments, a proximal end of a lead is configured and arranged for insertion into a connector receptacle disposed in a control module. FIG. 3A is a schematic view of one embodiment of a proximal end 304 of a lead 306 and a control module 102 of an electrical stimulation system. In FIG. 3A, the control module 102 includes a housing 114 in which a connector receptacle 144 is disposed. The connector receptacle 144 having conductive contacts 302 into which a proximal end 304 of the lead 306 with contact terminals 308 can be inserted, as shown by directional arrow 310, to electrically couple the control module 102 to the electrodes (134 of FIG. 1) at a distal end of the lead 306. Examples of connector receptacles in control modules are found in, for example, U.S. Pat. No. 7,244,150 and U.S. patent application Ser. No. 11/532,844, which are incorporated by reference. Contact terminals and conductive contacts can be in any suitable structures that can be configured and arranged for coupling the electrodes to the control module.

Figure 3B:
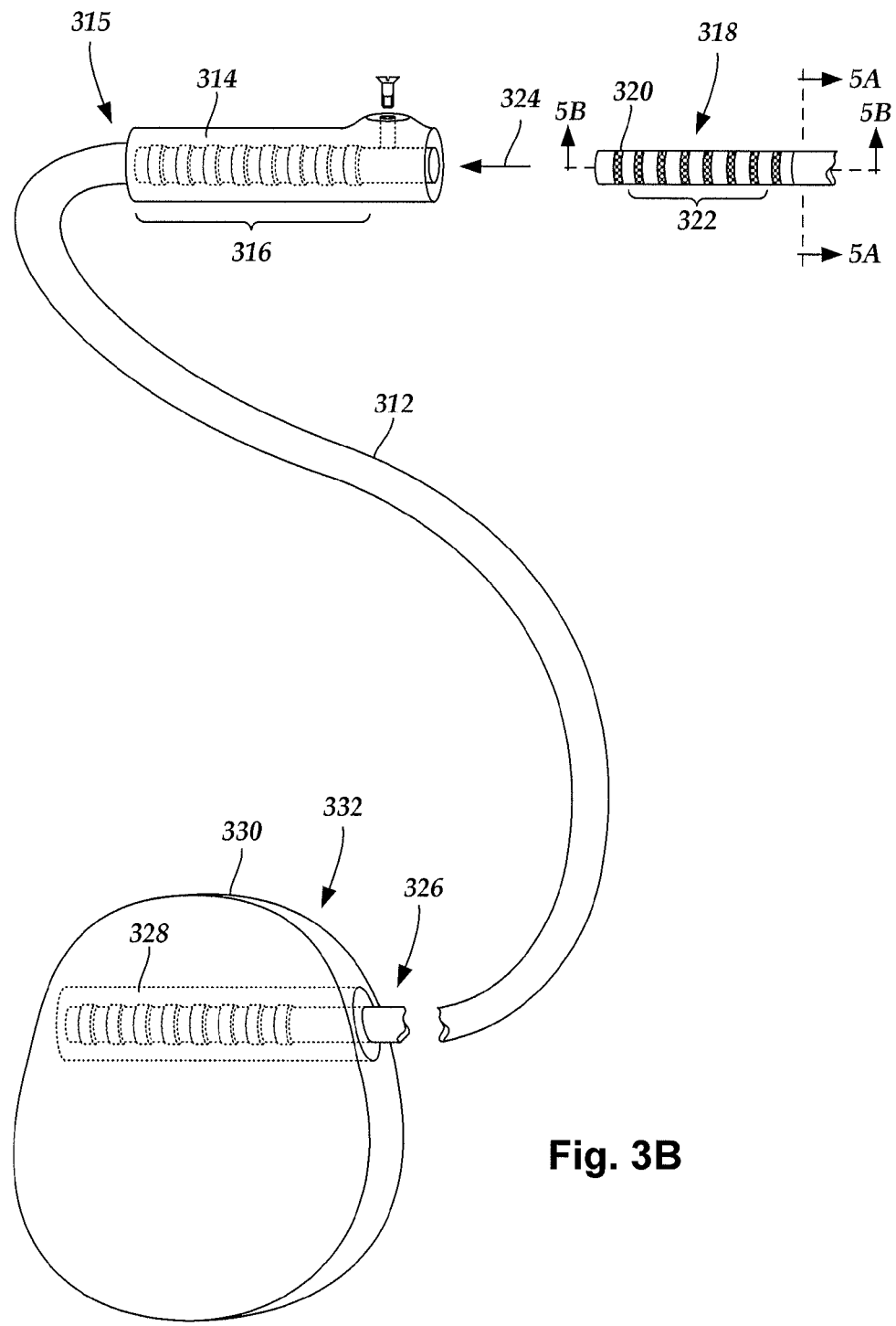
FIG. 3B is a schematic view of one embodiment of a proximal portion of a lead and a lead extension for an electrical stimulation system, according to the invention.

In other embodiments, a proximal end of a lead is configured and arranged for insertion into a connector receptacle disposed in a lead extension. FIG. 3B is a schematic view of one embodiment of a proximal portion of a lead and a lead extension for an electrical stimulation system. In FIG. 3B, a lead extension 312 includes a connector receptacle 314 disposed at a distal end 315 of the lead extension 312. The connector receptacle 314 includes conductive contacts 316 into which a proximal end 318 of a lead 320 with contact terminals 322 can be inserted, as shown by directional arrow 324, to electrically couple the lead extension 312 to the electrodes (134 in FIG. 1) at a distal end of the lead 320.

In at least some embodiments, the proximal end of a lead extension is similar to the proximal end of a lead. The lead extension 312 may include a plurality of conductive wires (not shown) that are electrically coupled to the conductive contacts 316 and that extend to a proximal end 326 of the lead extension 312 that is opposite to the distal end 315. In at least some embodiments, the conductive wires disposed in the lead extension 312 can be electrically coupled to a plurality of contact terminals disposed on the proximal end 326 of the lead extension 312. In at least some embodiments, the proximal end 326 of the lead extension 312 is configured and arranged for insertion into a connector receptacle disposed in another lead extension. In other embodiments, the proximal end 326 of the lead extension 312 is configured and arranged for insertion into a connector receptacle disposed in a control module. For example, in FIG. 3B the proximal end 326 of the lead extension 312 is inserted into a connector receptacle 328 disposed in a housing 330 of a control module 332.

Figure 4:
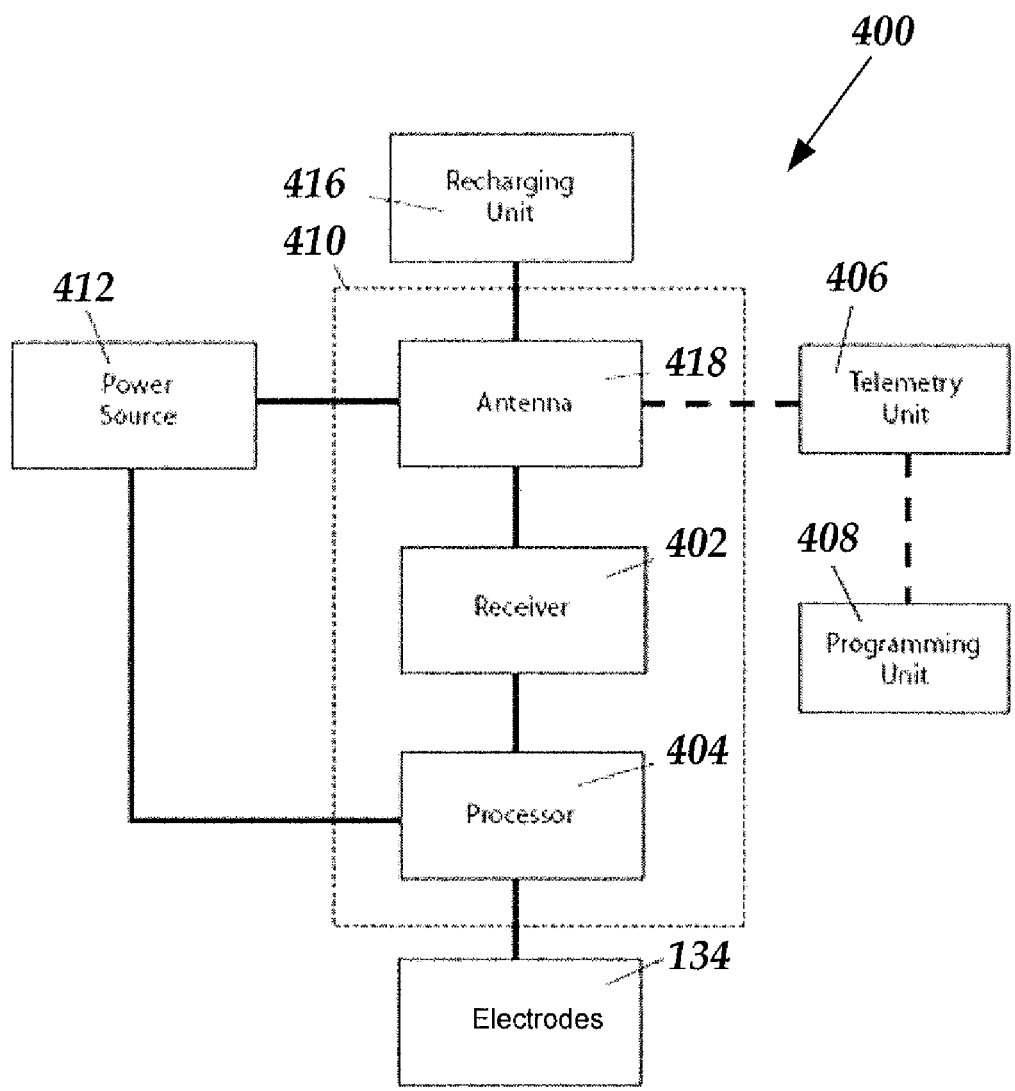
FIG. 4 is a schematic overview of one embodiment of components of a stimulation system, including an electronic subassembly disposed within a control module, according to the invention.

FIG. 4 is a schematic overview of one embodiment of components of an electrical stimulation system 400 including an electronic subassembly 410 disposed within a control module. It will be understood that the electrical stimulation system can include more, fewer, or different components and can have a variety of different configurations including those configurations disclosed in the stimulator references cited herein.

Some of the components (for example, power source 412, antenna 418, receiver 402, and processor 404) of the electrical stimulation system can be positioned on one or more circuit boards or similar carriers within a sealed housing of an implantable pulse generator, if desired. Any power source 412 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 418 or a secondary antenna. The external power source can be in a device that is mounted on the skin of the user or in a unit that is provided near the user on a permanent or periodic basis.

If the power source 412 is a rechargeable battery, the battery may be recharged using the optional antenna 418, if desired. Power can be provided to the battery for recharging by inductively coupling the battery through the antenna to a recharging unit 416 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 404 is generally included to control the timing and electrical characteristics of the electrical stimulation system. For example, the processor 404 can, if desired, control one or more of the timing, frequency, strength, duration, and waveform of the pulses. In addition, the processor 404 can select which electrodes can be used to provide stimulation, if desired. In some embodiments, the processor 404 may select which electrode(s) are cathodes and which electrode(s) are anodes. In some embodiments, the processor 404 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 408 that, for example, allows modification of pulse characteristics. In the illustrated embodiment, the processor 404 is coupled to a receiver 402 which, in turn, is coupled to the optional antenna 418. This allows the processor 404 to receive instructions from an external source to, for example, direct the pulse characteristics and the selection of electrodes, if desired.

In one embodiment, the antenna 418 is capable of receiving signals (e.g., RF signals) from an external telemetry unit 406 which is programmed by a programming unit 408. The programming unit 408 can be external to, or part of, the telemetry unit 406. The telemetry unit 406 can be a device that is worn on the skin of the user or can be carried by the user and can have a form similar to a pager, cellular phone, or remote control, if desired. As another alternative, the telemetry unit 406 may not be worn or carried by the user but may only be available at a home station or at a clinician's office. The programming unit 408 can be any unit that can provide information to the telemetry unit 406 for transmission to the electrical stimulation system 400. The programming unit 408 can be part of the telemetry unit 406 or can provide signals or information to the telemetry unit 406 via a wireless or wired connection. One example of a suitable programming unit is a computer operated by the user or clinician to send signals to the telemetry unit 406.

The signals sent to the processor 404 via the antenna 418 and receiver 402 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 400 to cease operation, to start operation, to start charging the battery, or to stop charging the battery. In other embodiments, the stimulation system does not include an antenna 418 or receiver 402 and the processor 404 operates as programmed.

Optionally, the electrical stimulation system 400 may include a transmitter (not shown) coupled to the processor 404 and the antenna 418 for transmitting signals back to the telemetry unit 406 or another unit capable of receiving the signals. For example, the electrical stimulation system 400 may transmit signals indicating whether the electrical stimulation system 400 is operating properly or not or indicating when the battery needs to be charged or the level of charge remaining in the battery. The processor 404 may also be capable of transmitting information about the pulse characteristics so that a user or clinician can determine or verify the characteristics.

Figure 5A:
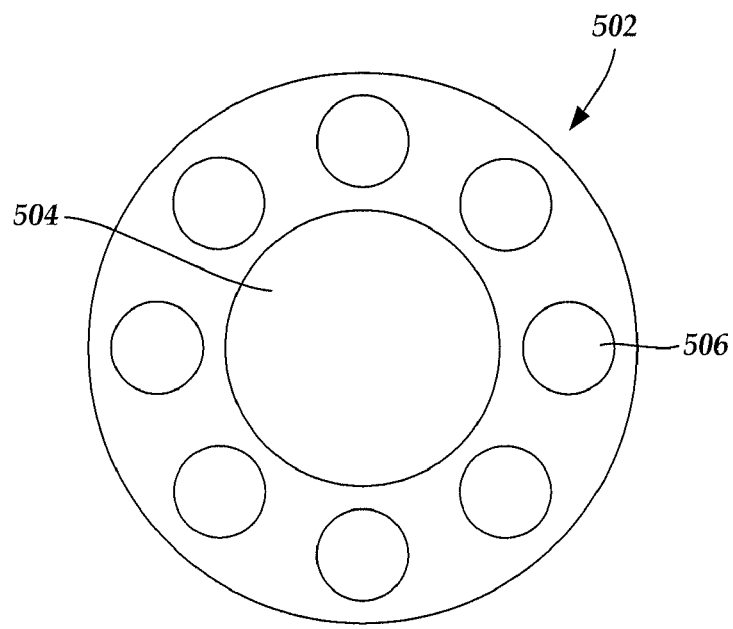
FIG. 5A is a schematic lateral cross-sectional view of one embodiment of a proximal portion of a lead, according to the invention.
Figure 5B:
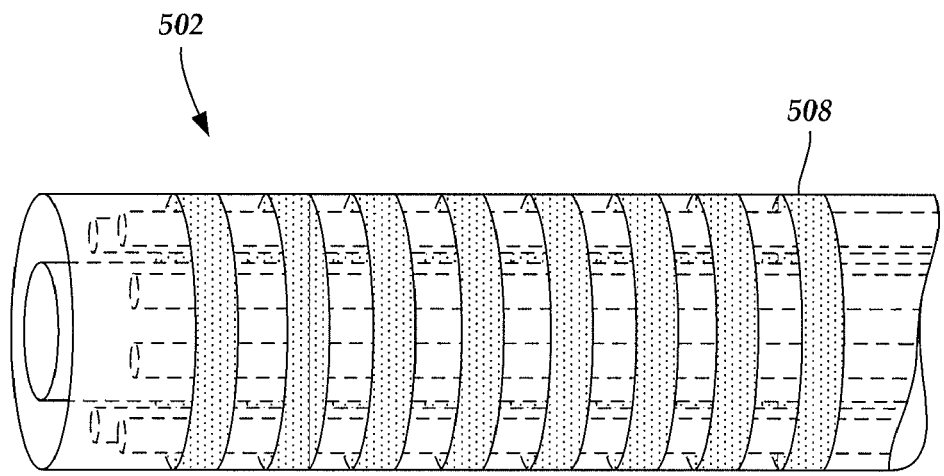
FIG. 5B is a schematic perspective view of the embodiment of the proximal portion of the lead shown in FIG. 3A, according to the invention.

FIG. 5A is a schematic lateral cross-sectional view of one embodiment of a proximal portion of a lead 502. In this embodiment, the proximal portion of the lead 502 includes a central lumen 504 and a plurality of peripheral lumens, such as peripheral lumen 506, disposed in the lead 502 lateral to the central lumen 504. In alternate embodiments, other arrangements of lumens are disposed in the lead with more or fewer lumens. In yet other alternate embodiments, the lead does not include any other lumens besides the central lumen. FIG. 5B is a schematic perspective view of the embodiment of the proximal portion of the lead 502 shown in FIG. 5A. The lead 502 includes contact terminals, such as contact terminal 508, disposed on the proximal portion of the lead 502. Contact terminals can be many different shapes and disposed in many different orientations suitable for electrically coupling to connective contacts. For example, as shown in FIG. 5B, the contact terminals are ring-shaped and evenly spaced on the proximal portion of the lead 502. The number of contact terminals can vary. For example, there may be two, four, six, eight, ten, twelve, sixteen, or more contact terminals. The contact terminals can be disposed in many different regular or irregular patterns with variable spacing between adjacent contact terminals. In a preferred embodiment, the positioning of the contact terminals match with the positioning of connective contacts in a connector receptacle.

Figure 5C:
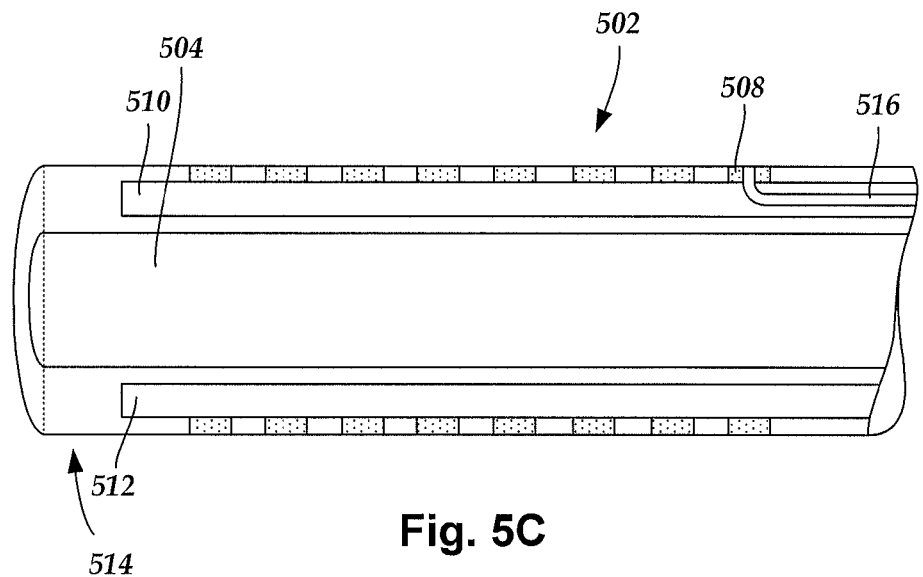
FIG. 5C is a schematic longitudinal cross-sectional view of the embodiment of the proximal portion of the lead shown in FIG. 3A, according to the invention.

FIG. 5C is a schematic longitudinal cross-sectional view the embodiment of the proximal portion of the lead 502 shown in FIG. 5A. The lead 502 includes the central lumen 504 and peripheral lumens 510 and 512. The central lumen 504 extends from a proximal end 514 of the lead 502. A plurality of conductor wires extend from electrodes (not shown) on a distal end of the lead 502 to contact terminals disposed on the proximal end 514 of the lead 502. The plurality of conductor wires may extend the entire length, or nearly the entire length, of the lead 502. Conductor wires can extend through one or more lumens or be embedded in the non-conductive material of the lead 502. In at least some embodiments, conductor wires are disposed in peripheral lumens. For example, FIG. 5B shows a conductor wire 516 disposed in the peripheral lumen 510 and electrically coupled to the contact terminal 508. It will be understood that there are additional conductors (not shown for clarity) which are electrically coupled to the other contact terminals. In at least some embodiments, the proximal end of a lead and the proximal end of a lead extension are similar in shape and size and relative contact-terminal shape, size, and positioning.

Figure 6A:
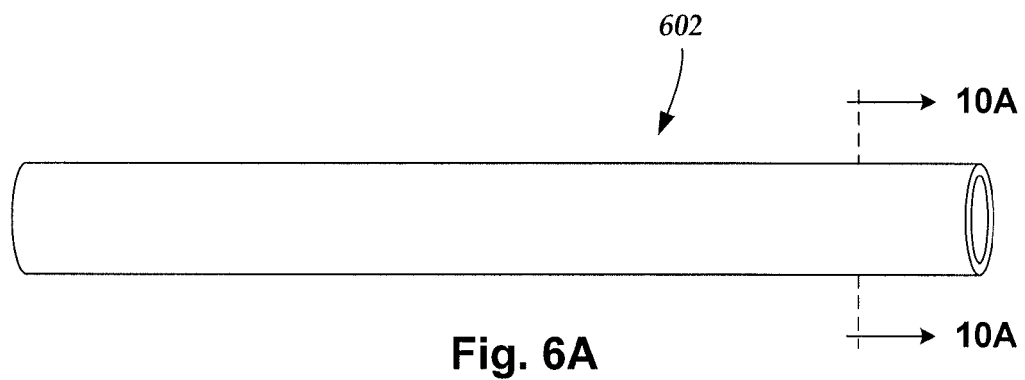
FIG. 6A is a schematic perspective view of one embodiment of a connector receptacle, according to the invention.

In at least some embodiments, a proximal end of a lead can be inserted into a connector receptacle. In other embodiments, a proximal end of a lead extension can be inserted into a connector receptacle. As discussed above, in at least some embodiments, connector receptacles can be in a lead extension or a control module. Connector receptacles can be many different shapes and sizes suitable for implantation and also configured and arranged to receive leads or lead extensions. For example, in FIG. 6A one embodiment of a connector receptacle 602 is shown that is tubular-shaped and is configured and arranged to receive the proximal end of either a lead or a lead extension.

Figure 6B:
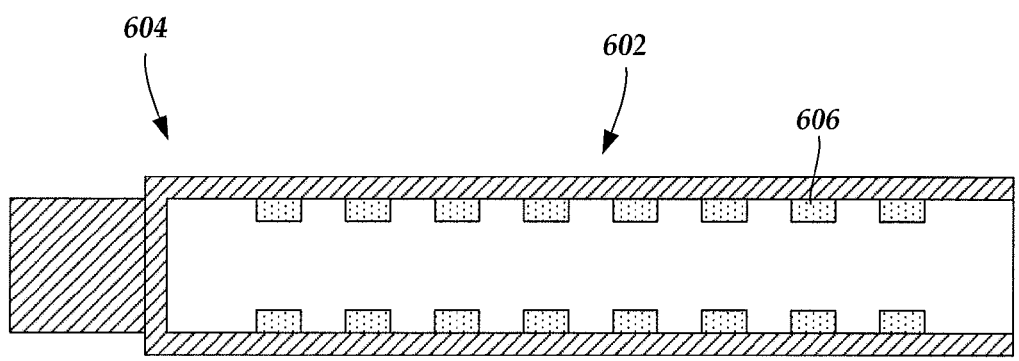
FIG. 6B is a schematic longitudinal cross-sectional view of the connector receptacle shown in FIG. 6A disposed in a lead extension, according to the invention.
Figure 6C:
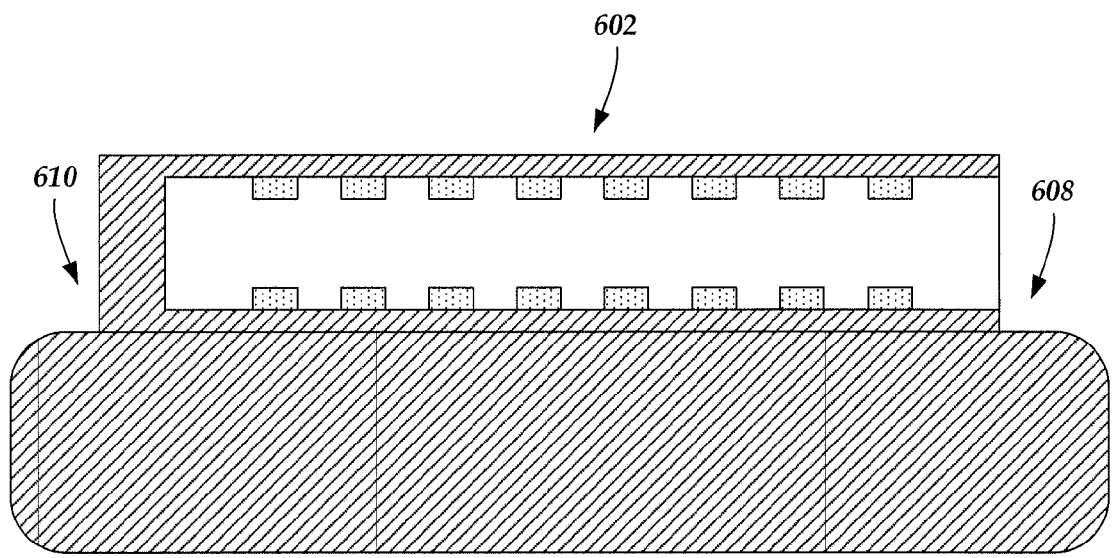
FIG. 6C is a schematic longitudinal cross-sectional view of the connector receptacle shown in FIG. 6A disposed in a control module, according to the invention.

The connector receptacle 602 can be disposed in a distal end of a lead extension. FIG. 6B shows a schematic longitudinal cross-sectional view of the connector receptacle 602 disposed in a distal end of a lead extension 604. A plurality of spaced-apart connective contacts, such as connective contact 606, are disposed on an interior surface of the connector receptacle 602. Alternately, the connector receptacle 602 can be disposed in a housing of a control module. FIG. 6C shows a schematic longitudinal cross-sectional view of the connector receptacle 602 disposed in a housing 608 of a control module 608.

Figure 7A:
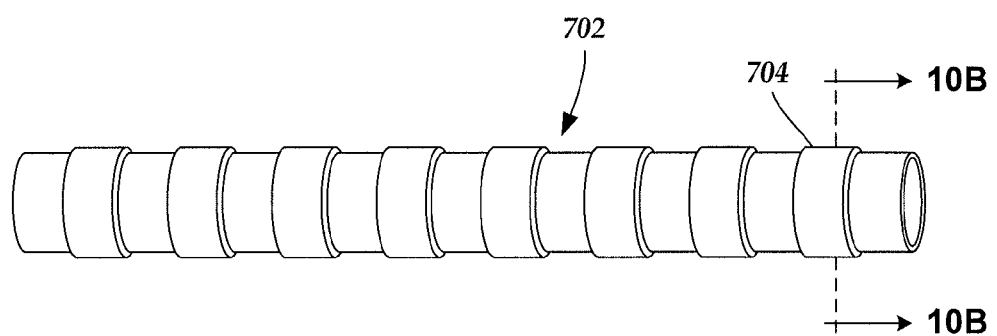
FIG. 7A is a schematic perspective view of a second embodiment of a connector receptacle, according to the invention.
Figure 7B:
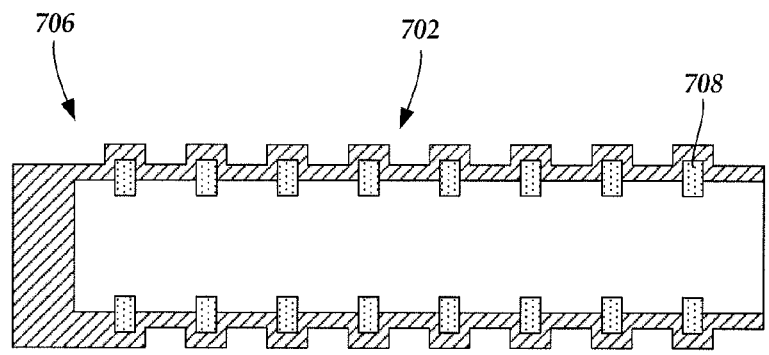
FIG. 7B is a schematic longitudinal cross-sectional view of the connector receptacle shown in FIG. 7A disposed in a lead extension, according to the invention.
Figure 7C:
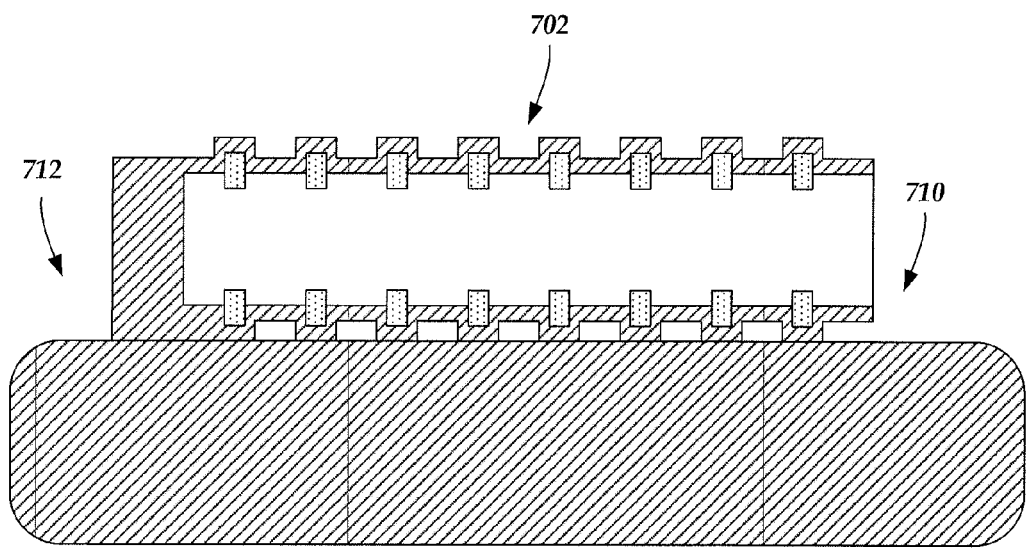
FIG. 7C is a schematic longitudinal cross-sectional view of the connector receptacle shown in FIG. 7A disposed in a control module, according to the invention.

In at least some embodiments, spaced-apart connective contacts are disposed in connector pockets in a connector receptacle. For example, in FIG. 7A one embodiment of a connector receptacle 702 is shown that includes a plurality of connector pockets, such as connector pocket 704, disposed on the connector receptacle 702. The number of connector pockets can vary. For example, there may be two, four, six, eight, ten, twelve, sixteen, or more connector pockets. The connector pockets can be spaced-apart in many different regular or irregular patterns with variable spacing between adjacent connector pockets. In a preferred embodiment, the positioning of the connector pockets correspond with the positioning of contact terminals on the proximal end of either a lead, such as the lead 320 or the lead 502, or a proximal end of a lead extension, such as the proximal end 326 of the lead extension 312. FIG. 7B shows a schematic longitudinal cross-sectional view of the connector receptacle 702 disposed in a distal end of a lead extension 706. A plurality of spaced-apart connective contacts, such as connective contact 708, are disposed on an interior surface of the connector receptacle 702. Alternately, the connector receptacle 602 can be disposed in a housing of a control module. FIG. 7C shows a schematic longitudinal cross-sectional view of the connector receptacle 702 disposed in a housing 710 of a control module 712.

Figure 8A:
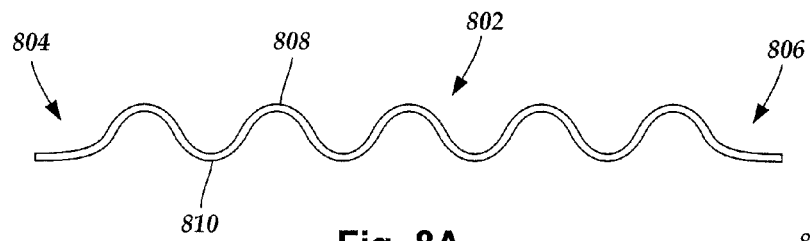
FIG. 8A is a schematic side view of one embodiment of a leaf spring connective contact, according to the invention.

In at least some embodiments, contact terminals on leads (or lead extensions) inserted in connector receptacles can be electrically coupled to one or more leaf spring conductive contacts within the connector receptacles. FIG. 8A is a schematic side view of one embodiment of a leaf spring connective contact 802. The leaf spring connective contact 802 includes a first end 804, a second end 806, and alternating ridges, such as ridge 808, and grooves, such as groove 810.

Figure 8B:
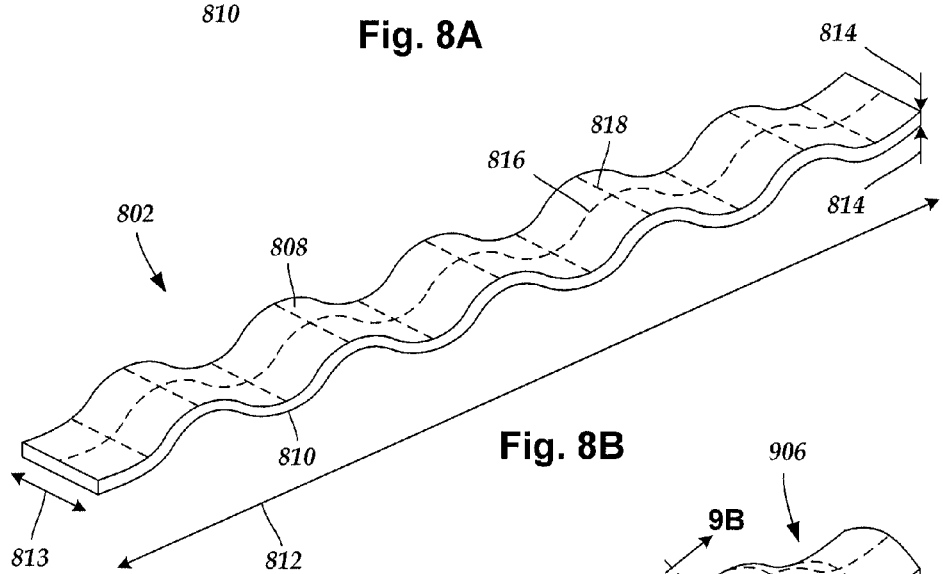
FIG. 8B is a schematic perspective view of the leaf spring connective contact shown in FIG. 8A, according to the invention.

FIG. 8B shows a schematic perspective view of the leaf spring connective contact 802. The leaf spring connective contact 802 has an elongated shape. Leaf spring connective contacts can be formed in many different elongated shapes, such as elongated rectangular, elongated oval, elongated hexagonal-shaped, and the like. For example, the leaf spring connective contact 802 shown in FIGS. 8A-8B is an elongated rectangular shape, with a longitudinal length 812 (represented in FIG. 8B by a double-headed arrow) that is substantially greater than both a lateral length 813 (represented in FIG. 8B as a double-headed arrow) and a thickness 814 (represented in FIG. 8B as two inward-facing arrows). The lengths 812-814 of the leaf spring connective contact can be made using any suitable length. In at least some embodiments, the lateral length 813 is greater than the thickness 814. In at least some embodiments, one or more of the lengths may not be constant. For example, the leaf spring connective contact may include one or more lateral portions that are wider or narrower than other lateral portions.

In at least some embodiments, the leaf spring connective contact is corrugated. In at least some embodiments, a corrugated leaf spring connective contact includes a plurality of alternating ridges and grooves. A corrugated pattern of alternating ridges and grooves may vary in shape, spacing, size, and number of ridges and grooves. For example, a ridge may include many different shapes. For example, a ridge can be rounded, V-shaped, rectangular-shaped, and the like. Similarly, a groove may also include many different shapes. For example, a groove can also be rounded, V-shaped, rectangular-shaped, and the like. Alternating ridges and grooves may include ridges and grooves that are either similarly-shaped or dissimilarly-shaped.

In at least some embodiments, a leaf spring connective contact may have substantially flat portions between alternating ridges and grooves. In at least some embodiments, the lengths of the substantially flat portions may be the same as other substantially flat portions or may be different. The sizes of the alternating ridges and grooves may vary. In at least some embodiments, the ridges and the grooves are the same size, while, in at least some other embodiments, the size of one or more of the ridges are different from each other or from the size of one or more of the grooves, which also may vary in size from each other. The leaf spring connective contact can be made with any suitable number of alternating ridges and grooves. The number of ridges may be equal to the number of grooves on a leaf spring connective contact, or the number of ridges may be equal to the number of grooves plus or minus one. For example, a leaf spring connective contact may contain one ridge and one groove, one ridge and two grooves, two ridges and one groove, two ridges and two grooves, two ridges and one groove, two ridges and three grooves, three ridges and three grooves, four ridges and four grooves, five ridges and five grooves, five ridges and four grooves, five ridges and six grooves, six ridges and seven grooves, ten ridges and ten grooves, ten ridges and eleven grooves, ten ridges and nine grooves, or some other combination of numbers of ridges and grooves. For example, in FIGS. 8A-8B, the alternating ridges are evenly spaced, rounded and have five ridges and four grooves.

In FIG. 8B a dashed longitudinal contour line 816 is shown for clarity of illustration to show the longitudinal contour of the leaf spring connective contact 802. Additionally, a plurality of dashed lateral contour lines, such as dashed lateral contour line 818, are shown at various locations along the longitudinal length of the leaf spring connective contact 802, for clarity of illustration, to show the lateral contour of the leaf spring connective contact 802 at various locations along the length of the leaf spring connective contact 802.

Figure 9A:
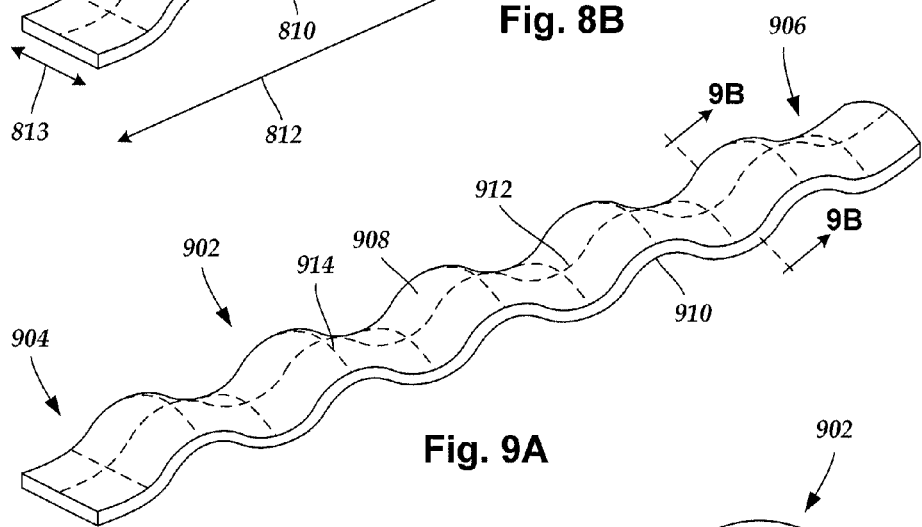
FIG. 9A is a schematic perspective view of a second embodiment of a leaf spring connective contact, according to the invention.
Figure 9B:
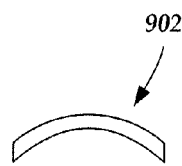
FIG. 9B is a schematic lateral cross-sectional view of the leaf spring connective contact shown in FIG. 9A, according to the invention.

In at least some embodiments, at least a portion of the lateral length is curved. For example, the lateral length may include one or more ridges or grooves. FIG. 9A is a schematic perspective view of a second embodiment of a leaf spring connective contact 902. The leaf spring connective contact 902 includes a first end 904, a second end 906, and is corrugated, with a plurality of alternating ridges, such as ridge 908, and grooves, such as groove 910. For clarity of illustration, FIG. 9A includes a dashed longitudinal contour line 912 and a plurality of dashed lateral contour lines, such as dashed lateral contour line 914. In the embodiment shown in FIG. 9A, a ridge extends along substantially the entire longitudinal length of the leaf spring connective contact. However, the first end 904 is relatively flat. FIG. 9B shows a schematic lateral cross-sectional view of the leaf spring connective contact 902. As discussed below, in at least some embodiments, the first end is flat to facilitate attachment of the leaf spring connective contact to a connector receptacle. Also discussed below, in at least some embodiments, one or more ridges or grooves extending along one or more portions of the longitudinal length of the leaf spring connective contact may facilitate forming a desired level of resistance for insertion and retention of a lead or lead extension into a connector receptacle.

A leaf spring connective contact can be formed using any non-corrosive, conductive material suitable for implantation. Examples of suitable materials include metals, alloys, conductive polymers, conductive carbon, and the like, as well as combinations thereof. In several preferred embodiments, a leaf spring connective contact is formed from platinum/iridium (80/20) or (90/10). Other preferred metals and alloys include titanium, MP35N® alloy, low-carbon stainless steel (such as 316L stainless steel), pure platinum, and iridium-coated metals. The leaf spring connective contact may be formed in a desired shape by any process including, for example, molding (including injection molding), casting, and the like. In at least some embodiments, the leaf spring connective contacts can have suitable spring constants which may affect the degree of flexibility of the leaf spring connective contact. The flexibility may also be affected by the type of material used to form the leaf spring connective contact.

In at least some embodiments, a plurality of spaced-apart leaf spring connective contacts can be disposed in a connector receptacle and electrically coupled to an electronic subassembly disposed in a control module. In at least some embodiments, one or more of the leaf spring connective contacts disposed in the connector receptacle can be configured and arranged to receive a proximal end of a lead or a lead extension. The number of leaf spring connective contacts disposed in a connector receptacle can vary. For example, there may be two, four, six, eight, ten, twelve, sixteen, or more leaf spring connective contacts. The leaf spring connective contacts can be spaced apart in many different regular or irregular patterns with variable spacing between adjacent leaf spring connective contacts. In a preferred embodiment, the positioning of the leaf spring connective contacts match with the positioning of contact terminals on the proximal end of a lead (or a lead extension) desired for insertion in the connector receptacle.

Figure 10A:
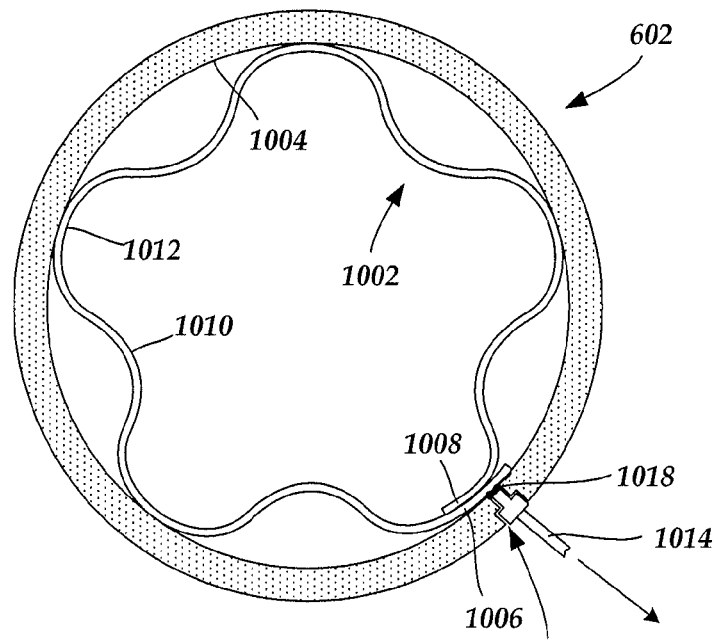
FIG. 10A is a schematic lateral cross-sectional view of one embodiment of a leaf spring connective contact disposed in the connector receptacle shown in FIG. 6A, according to the invention.

In at least some embodiments, each leaf spring connective contact is wrapped around at least a portion of an inner surface of the connector receptacle. In at least some embodiments, each leaf spring connective contact is wrapped around the entire inner surface of the connector receptacle with a first end of the leaf spring connective contact contacting a second end of the leaf spring connective contact. FIG. 10A is a schematic lateral cross-sectional view of one embodiment of a leaf spring connective contact 1002 disposed in the connector receptacle 602 shown in FIG. 6A. In FIG. 10A, the leaf spring connective contact 1002 is shown wrapped around an inner surface 1004 of the connector receptacle 1002. The leaf spring connective contact includes a first end 1006, a second end 1008, and alternating ridges, such as ridge 1010, and grooves, such as groove 1012. A conductor 1014 is electrically coupled to the leaf spring connective contact 1002 and extends through a connection port 1016 defined in the connector receptacle 602. In at least some embodiments, the conductor 1014 couples electronically to an electronic subassembly of a control module. In other embodiments, the conductor 1014 couples electronically to one or more contact terminals, which, in turn are configured and arranged to couple electrically with an electronic subassembly of a control module.

In at least some embodiments, leaf spring connective contacts are held in a fixed location within a connector receptacle. In at least some embodiments, the leaf spring connective contacts are attached to the inner surface 1004 of the connector receptacle. In a preferred embodiment, the leaf spring connective contacts are spaced-apart in a pattern that corresponds with the spacing of contact terminals on a proximal end of a lead (or lead extension). The leaf spring connective contacts can be held in place in many different ways. For example, the leaf spring connective contacts can be attached to connector receptacle by one or more of spot welding, laser welding, adhesive, soldering, epoxy, or the like. In at least some embodiments, the leaf spring connective contacts are held in place by electrically coupling each leaf spring conductive contact to a corresponding conductor by one or more of, for example, spot welding, laser welding, soldering, or the like. In FIG. 10A, the first end 1006 of the leaf spring connective contact 1002 is shown attached to the conductor 1014 by spot welding 1018. Additionally, the spot welding 1018 is also electrically coupling the conductor 1014 to the leaf spring connective contact 1002. In at least some embodiments, the leaf spring connective contacts are attached to the connector receptacle in one or more other locations, either instead of, or in addition to, the attachment at the first end to the conductor 1014, such as by adhering one or more of the grooves to the inner surface 1004 of the connector receptacle 602. It is preferred that the region of each leaf spring connective contact attached to the connector receptacle have a substantially flat region to adequately affix the leaf spring connective contact to the connector receptacle. For example, the embodiments of the leaf spring connective contact shown in FIGS. 8A-9B included a relatively flat first end. In at least some embodiments, grooves include substantially flat regions for facilitating attachment to the connector receptacle 602. In at least some embodiments, the second end 1008 is attached to the first end 1006.

Figure 10B:
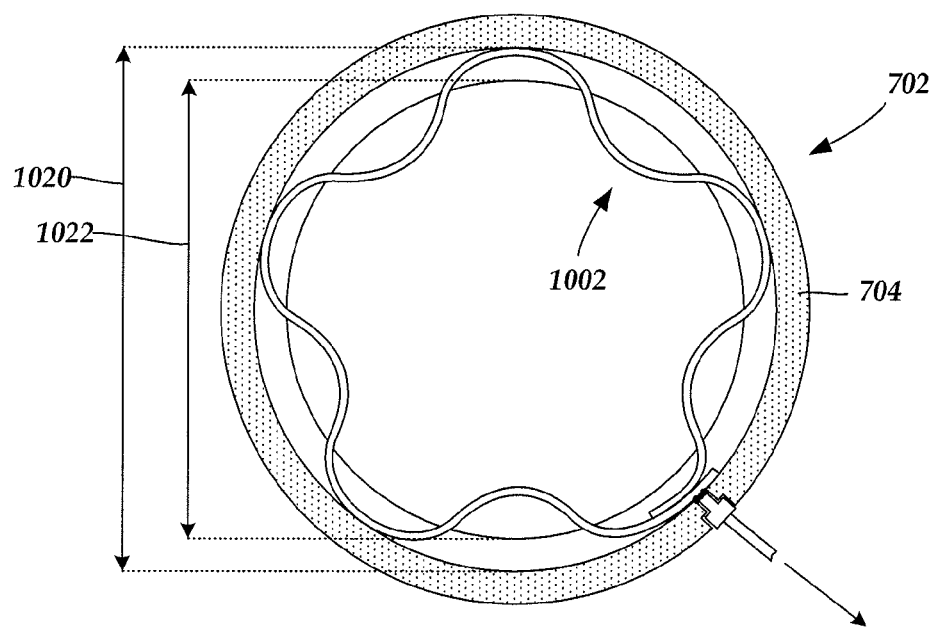
FIG. 10B is a schematic lateral cross-sectional view of one embodiment of a leaf spring connective contact disposed in the connector receptacle shown in FIG. 7A, according to the invention.

In at least some embodiments, leaf spring connective contacts are held in a fixed location within a connector receptacle, at least in part, by positioning each leaf spring contact within a connector pocket. FIG. 10B is a schematic lateral cross-sectional view of one embodiment of a leaf spring connective contact 1002 disposed in the connector receptacle 1004 shown in FIG. 7A. In FIG. 10B, the leaf spring connective contact 1002 is disposed in the connector pocket 704 of the connector receptacle 702. In at least some embodiments, the connector pocket is configured and arranged to hold the leaf spring connective contact in a fixed position by a shape variance between the connector pocket and the non-connector-pocket portions of the connector receptacle. For example, in FIG. 10B the connector pocket 704 has a diameter 1020 that is greater than the diameter 1022 of the non-connector-pocket portions of the connector receptacle 702. In at least some embodiments, the spring constant and the material used to form the leaf spring connective contact provide the stiffness necessary to maintain the leaf spring connective contact 1002 within the connector pocket 704. In at least some embodiments, the leaf spring connective contact is further held in position by being attached to the connector receptacle using one or more attachment mechanisms, such as one or more of the examples of attachments discussed above, with reference to FIG. 10A.

In at least some embodiments, when the proximal end of a lead or a lead extension is inserted into a connector receptacle with a plurality of spaced-apart leaf spring connective contacts, the ridges of the leaf spring connective contact make contact with the proximal end of the inserted lead or lead extension. In preferred embodiments, the leaf spring connective contacts are spaced-apart to match the spacing of contact terminals on the inserted lead or lead extension. Thus, when the lead or lead extension is inserted into the connector receptacle, one or more of the contact terminals on the lead or lead extension align with one or more leaf spring connective contacts. When the inserted lead or lead extension makes contact with a ridge, the ridge becomes sandwiched between the lead or lead extension and the connector receptacle and becomes deformed. The leaf spring connective contact thereby provides some resistance to insertion and can be used to hold the inserted lead or lead extension in place once inserted. The degree of resistance can be adjusted by adjusting the shape, size, and spring constant of the leaf spring connective contact, as well as adjusting the material from which the leaf spring connective contact is formed. For example, providing leaf spring connective contacts with one or more longitudinal ridges (see FIG. 8A) may decrease the amount of surface area of the spring leaf connective contacts making contact with inserted leads or lead extensions and, thereby, reduce the amount of resistance produced by the leaf spring connective contacts to inserted leads or lead extensions.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable control module of an electrical stimulation system, the implantable control module comprising:
    a housing defining a connector receptacle configured and arranged to receive a proximal end of a lead, the housing further defining within the connector receptacle region a plurality of spaced-apart leaf spring connective contacts, each leaf spring connective contact comprising an elongated body having a first end and an opposing second end, the leaf spring connective contact wrapped around at least a portion of an inner surface of the connector receptacle such that the first end and the second end overlap one another, wherein the connective contact is corrugated such that the connective contact comprises a plurality of alternating ridges and grooves;
    an electronic subassembly disposed in the housing; and
    a plurality of conductors, each conductor coupling the electronic subassembly with at least one of the leaf spring connective contacts.

2. The implantable control module of claim 1, wherein the ridges are configured and arranged to contact the proximal end of the lead when the proximal end of the lead is inserted in the connector receptacle and the grooves are configured and arranged to contact an inner surface of the connector receptacle.

3. The implantable control module of claim 1, wherein the connector receptacle further defines at least one connection port, at least one of the conductors extending through the at least one connection port.

4. The implantable control module of claim 1, wherein the connector receptacle further comprises a plurality of a connector pockets, and wherein at least one of the leaf spring connective contacts is disposed in each of the connector pockets.

5. The implantable control module of claim 1, wherein at least one of the leaf spring connective contacts has a lateral length that includes a ridge or a groove extending across the entire lateral length of the at least one leaf spring connective contact.

6. The implantable control module of claim 5, wherein the ridge or groove extending across the entire lateral length of the at least one leaf spring connective contact extends longitudinally along substantially entirely the length of the at least one leaf spring connective contact.

7. The implantable control module of claim 5, wherein the ridge or groove extending across the entire lateral length of the at least one leaf spring connective contact extends across the second end of the at least one leaf spring connective contact.

8. The implantable control module of claim 1, wherein the first end of the leaf spring connective contact is flat.

9. The implantable control module of claim 1, wherein the first end of at least one of the plurality of leaf spring connective contacts is coupled to the inner surface of the connector receptacle.

10. The implantable control module of claim 1, wherein at least one of the grooves of at least one of the plurality of leaf spring connective contacts is coupled to the inner surface of the connector receptacle.

11. The implantable control module of claim 1, wherein at least one of the leaf spring connective contacts further comprises at least one substantially flat portion disposed between one of the alternating ridges and grooves.

12. An electrical stimulating system comprising:
the implantable control module of claim 1; and
a lead having a proximal end and a distal end, wherein the proximal end of the lead is configured and arranged for insertion into the connector receptacle of the implantable control module, the lead comprising
a plurality of electrodes disposed on the distal end of the lead,
a plurality of contact terminals disposed on the proximal end of the lead, and
a plurality of conductor wires extending along the lead to couple the electrodes electrically to the contact terminals.

13. The electrical stimulation system of claim 12, wherein the connector receptacle is configured and arranged to sandwich at least one of the leaf spring conductive contacts between an inner surface of the connector receptacle and the proximal end of the lead when the proximal end of the lead is inserted into the connector receptacle.

14. The electrical stimulation system of claim 12, wherein the connector receptacle further defines at least one connection port, at least one conductor extending through the at least one connection port.

15. The electrical stimulation system of claim 12, wherein the connector receptacle further comprises a plurality of a connector pockets, and wherein at least one of the leaf spring connective contacts is disposed in each of the connector pockets.

16. An implantable control module of an electrical stimulation system, the implantable control module comprising:
a housing defining a connector receptacle configured and arranged to receive a proximal end of a lead, the housing further defining within the connector receptacle region a plurality of spaced-apart leaf spring connective contacts, each leaf spring connective contact being corrugated and wrapped around at least a portion of an inner surface of the connector receptacle;
an electronic subassembly disposed in the housing; and
a plurality of conductors, each conductor coupling the electronic subassembly with at least one of the leaf spring connective contacts, wherein the leaf spring connective contacts are welded to at least one of the conductors.

17. A method for stimulating patient tissue, the method comprising:
implanting a lead into a patient, the lead comprising a plurality of electrodes disposed on a distal end of the lead and electrically coupled to at least one contact terminal disposed on a proximal end of the lead;
disposing the proximal end of the lead into a connector comprising a plurality of leaf spring connective contacts coupled electrically to a control module, at least one leaf spring connective contact configured and arranged to couple electrically with at least one contact terminal, each leaf spring connective contact comprising an elongated body having a first end and an opposing second end, the leaf spring connective contact wrapped around at least a portion of an inner surface of the connector receptacle such that the first end and the second end overlap one another, wherein the connective contact is corrugated such that the connective contact comprises a plurality of alternating ridges and grooves; and
providing electrical signals from the control module to electrically stimulate patient tissue using at least one of the electrodes.

18. The method of claim 17, wherein disposing the proximal end of the lead into the connector comprises the connector being disposed in the control module.

19. The method of claim 17, wherein disposing the proximal end of the lead into the connector comprises the connector being disposed in a lead extension, the lead extension configured and arranged to couple electrically to the control module.

20. An implantable lead extension of an electrical stimulation system, the implantable lead extension comprising:
a housing disposed at a distal end of the lead extension, the housing defining a connector receptacle configured and arranged to receive a proximal end of a lead, the housing further defining within the connector receptacle region a plurality of spaced-apart leaf spring connective contacts, each leaf spring connective contact comprising an elongated body having a first end and an opposing second end, the leaf spring connective contact wrapped around at least a portion of an inner surface of the connector receptacle such that the first end and the second end overlap one another, wherein the connective contact is corrugated such that the connective contact comprises a plurality of alternating ridges and grooves;
a plurality of terminal contacts disposed at a proximal end of the lead extension; and
a plurality of conductors, each conductor coupling at least one of the leaf spring connective contacts with at least one of the terminal contacts.

21. The electrical stimulation system of claim 20, wherein the proximal end of the lead extension is configured and arranged to couple to a control module.

* * * * *